(12) United States Patent
Schmidt et al.

(10) Patent No.: US 7,417,003 B2
(45) Date of Patent: Aug. 26, 2008

(54) SOLID ACID CATALYST AND PROCESS FOR DECOMPOSITION OF CUMENE HYDROPEROXIDE

(75) Inventors: Robert J. Schmidt, Barrington, IL (US); Deng-Yang Jan, Elk Grove Village, IL (US); Raelynn M. Miller, LaGrange, IL (US); James A. Johnson, Clarendon Hills, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 11/648,844

(22) Filed: Dec. 29, 2006

(65) Prior Publication Data

US 2008/0161181 A1    Jul. 3, 2008

(51) Int. Cl.
   *B01J 29/06*    (2006.01)
(52) U.S. Cl. .......................................... 502/63; 502/64
(58) Field of Classification Search .................. 502/63, 502/64
   See application file for complete search history.

(56) References Cited

U.S. PATENT DOCUMENTS

| 6,376,730 | B1 * | 4/2002 | Jan et al. | 585/467 |
| 6,649,802 | B1 * | 11/2003 | Frame et al. | 585/533 |
| 2006/0266673 | A1 * | 11/2006 | Rende et al. | 208/120.1 |
| 2006/0270865 | A1 * | 11/2006 | Wang et al. | 554/174 |

FOREIGN PATENT DOCUMENTS

| DE | 10110521 | 9/2002 |
| EP | 492807 | 7/1992 |
| JP | 62114922 | 5/1987 |
| JP | 2004-352674 | 12/2004 |
| SU | 992508 | 1/1983 |
| WO | WO 9408932 | 4/1994 |
| WO | WO 06015826 | 2/2004 |

OTHER PUBLICATIONS

Selvin, Rosilda; Rajarajeswari, G.R.; Selva Roselin, L.; Sadasivam, V.; Sivasankar, B; Rengaraj, K., *Catalytic decomposition of cumene hydroperoxide into phenol and acetone*, 2001, Applied Catalysts, A:, General (2001), 219(1-2), 125-129. Publisher: Elsevier Science B.V., no month.

Sasidharan, Manickam; Kumar, Rajiv, *Zeolite-cataclyzed selective decomposition of cumene hydroperoxide into phenol and acetone*, 1997, Journal of Chemical Research, Synopses (1997), (2), 52-53. Publisher: Royal Society of Chemistry, no month.

Kolesnikov, I.M., *Decomposition of Cumene Hydroperoxide in the Presence of Solid Catalysts*, 1989, Zhurnal Prikladnoi Khimii (Sankt-Peterburg, Russian Federation) (1989), 62(4), 818-24, no month.

Arsen'eva, N.S.; Kolesnikov, I.M.; Bruk, A. Yu., *Kinetic model of the heterolytic decomposition of cumene hydroperoxide to phenol and acetone in the presence of a sillimantie-zeolite-containing catalyst*, 1981, Zhurnal Prikladnoi Khimii (Sankt-Peterburg, Russian Federation) (1981), 54(8), 1793-9, no month.

Arsen'eva, N.S.; Bruk, A. Yu., *Decomposition of isopropylbenzene hydroperoixde on a sillimanite zeolite-containing catalyst*, 1979, Neftepererabotka i Neftekhimiya (Moscow, Russian Federation) (1979), (6), 10-11, no month.

Zhou, Jinkai; Du, Yingchun; Chen, Shu, *Deactivation and regeneration of zeolite catalysts for decomposition of cumene hydroperoxide*, 199, Gongye Cuihua (1999), 7(5), 18-23. Publisher: Gongye Cuihua Bianjibu. no month.

Zhou, Jinkai; Du, Yingchun; Chen, Shu, *Decomposition of cumene hydroperoxide over zeolite catalysts*, 1999, Shiyou Lianzhi Yu Huagong (1999), 30(6), 48-51. Publisher: Shiyou Lianzhi Yu Huangong Zazhishe. no month.

\* cited by examiner

*Primary Examiner*—Elizabeth D Wood
(74) *Attorney, Agent, or Firm*—James C Paschall

(57) ABSTRACT

The present invention provides a catalyst particle of an inner core, an outer layer surrounding and bonded to the inner core, the outer layer of a zeolite beta catalyst, and the outer layer having a volumetric fraction from about 0.17 to about 0.62 of the entire catalyst particle.

11 Claims, 3 Drawing Sheets

SOLID ACID CATALYST AND PROCESS FOR DECOMPOSITION OF CUMENE HYDROPEROXIDE

BACKGROUND OF THE INVENTION

The current process of choice for commercial phenol production utilizes the autocatalytic cumene/air oxidation to cumene hydroperoxide (CHP) route for over 50% of the world's production of phenol. A key step in this process is the decomposition (cleavage) of CHP produced in the oxidation section of the plant to phenol and acetone using dilute mineral acid ($H_2SO_4$) as an acid catalyst. Use of the liquid acid requires subsequent neutralization and purification of the phenol at substantial cost, and a waste stream generation that could be avoided if an effective solid acid catalyst could be used. CHP decomposition is a very exothermic reaction which is normally carried out on a commercial scale in continuous stirred or back-mixed reactors. In such reactors only a small fraction of CHP is unreacted at any given time and the reaction medium consists essentially of the products of decomposition of CHP, i.e., phenol and acetone, plus any solvent (e.g., cumene and/or recycle acetone) and other materials added with CHP to the reactor. During cumene oxidation small amounts of dimethylphenylcarbinol (DMPC) and acetophenone are also formed. In the presence of acid catalyst, DMPC dehydrates to alpha-methylstyrene (AMS), a useful by-product. Very high yields of AMS can be obtained from pure DMPC, e.g., 98% yield upon dehydration over acidic silica at 300° C. In the presence of phenol, however, and more specifically in a phenol/acetone/cumene mixture which is a solvent in the decomposition of CHP/DMPC mixtures, the ultimate AMS yield is normally about 50-60 mol % of the DMPC. Main by-products are AMS dimers and cumylphenol which have no commercial value. Formation of cumylphenol also reduces the phenol yield.

Although phenol and acetone have been produced by the decomposition of the cumene oxidation product for decades using a liquid mineral acid such as sulfuric acid as a catalyst, there is a continuing incentive to produce them at a lower cost and with a reduced by-product formation.

INFORMATION DISCLOSURE

U.S. Pat. No. 4,358,618 (Sifniades et al.) discloses a multi-step process for the production of acetone and phenol by the decomposition of cumene hydroperoxide.

U.S. Pat. No. 6,201,157 B1 (Keenan) discloses a process for the decomposition of cumene hydroperoxide using an acid catalyst and neutralizing the acid catalyst after the completion of the decomposition by the addition of an amine.

U.S. Pat. No. 6,307,112 (Weber et al.) discloses a process for cleaving cumene hydroperoxide wherein the mass flow ratio of a recycled partial product stream to the cumene hydroperoxide-containing feed stream sent to the cleavage reactor is less than 10. The patent discloses the use of vertical tube bundle heat exchangers.

U.S. Pat. No. 4,490,565 and U.S. Pat. No. 4,490,566 (Chang) disclose the production of phenol and acetone by the cleavage of cumene hydroperoxide in the presence of a solid heterogenous catalyst with acidic activity including, respectively, zeolite beta and ZSM-5.

European Patent Application Publication No. 0 492 807 A2 (Knifton) discloses the production of phenol and acetone by the cleavage of cumene hydroperoxide in the presence of a solid catalyst with acidic activity including the isostructural group of faujasite and zeolites X and Y.

U.S. Pat. No. 6,710,003 (Jan et al.) discloses the process for preparing attrition resistant zeolitic layered catalyst compositions.

BRIEF SUMMARY OF THE INVENTION

The present invention provides a catalyst particle of an inner core, an outer layer surrounding and bonded to the inner core, the outer layer of a zeolite beta catalyst, and the outer layer having a volumetric fraction from about 0.17 to about 0.62 of the entire catalyst particle.

The present invention further provides a catalyst particle having: (1) a core of a refractory inorganic oxide; and (2) a zeolite beta coating surrounding the core and with the outer layer having a volumetric fraction from about 0.17 to about 0.62 of the entire catalyst particle.

The present invention further provides a process for preparing a layered catalyst particle. The process includes: (1) providing an inner core; (2) providing a coating material of a beta zeolite; (3) providing a sol of a binder material; (4) preparing a slurry by mixing the coating material, the sol of the binder material and an organic bonding agent; (5) coating the inner core with the slurry to yield a coated core; (6) drying the coated core at a temperature from about 50° C. to about 300° C. to yield a dried coated core; and, (7) calcining the dried coated core at a temperature from about 400° C. to about 900° C. for a time sufficient to bond the coating material to the inner core to provide the layered catalyst particle having an outer layer taking up a volumetric ratio from about 0.17 to about 0.62 of the entire catalyst particle.

DETAILED DESCRIPTION OF THE INVENTION

Figure 1:
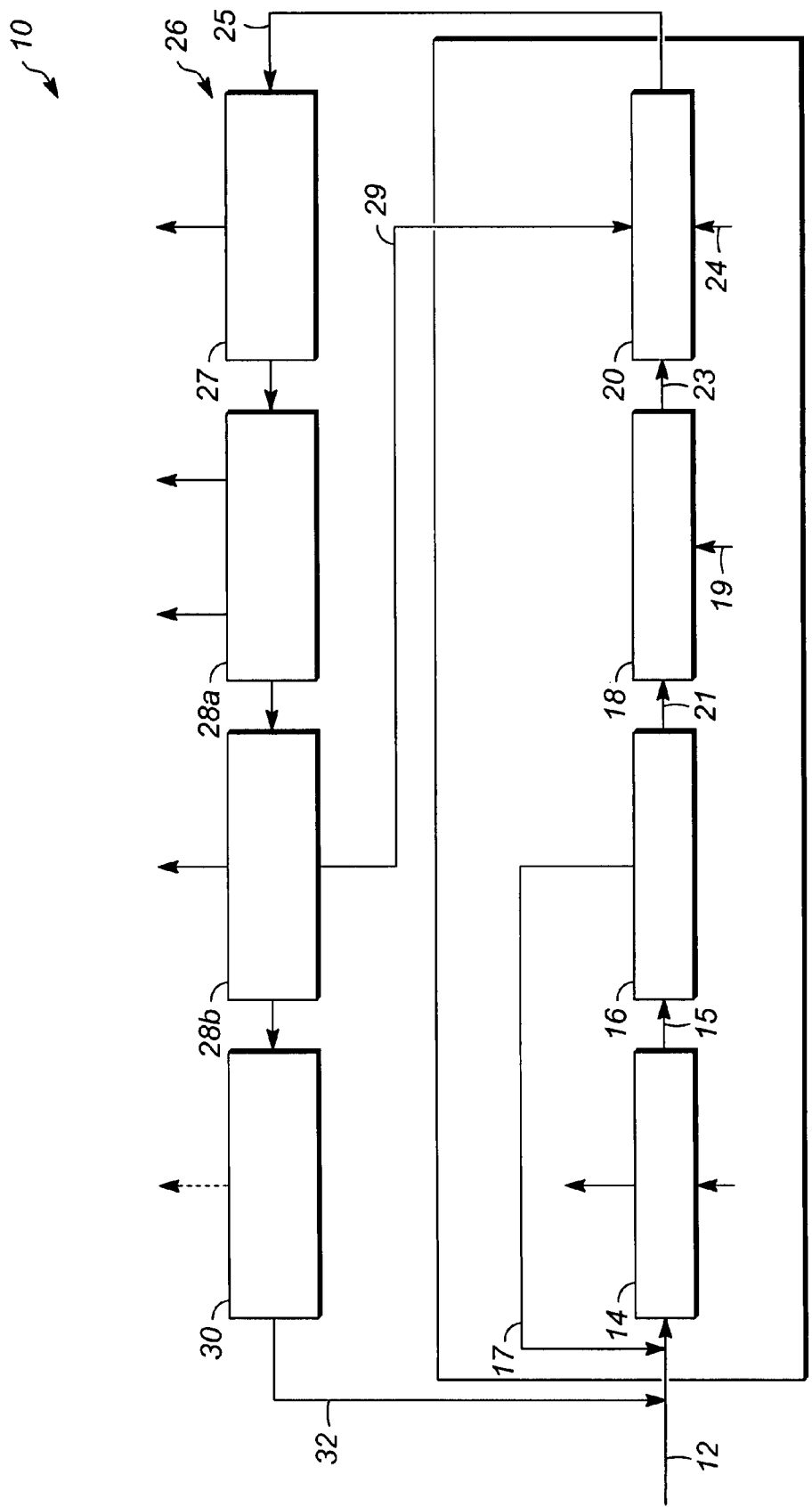
FIG. 1 shows a block flow diagram of a prior art process that utilizes the cumene peroxidation route to produce phenol.
Figure 2:
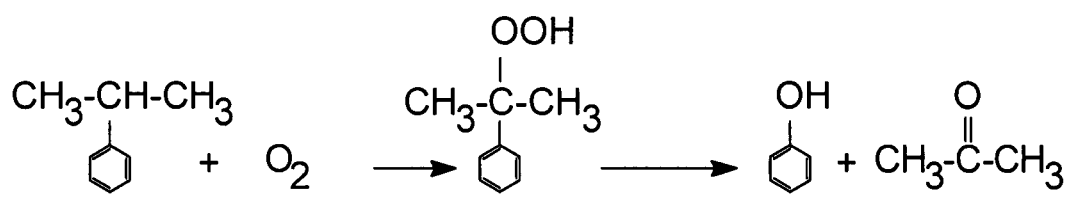
FIG. 2 shows the main reactions that occurs during the oxidation and decomposition steps of the prior art process.

FIG. 1 shows a block flow diagram 10 of a prior art process that utilizes the cumene peroxidation route to produce phenol. A supply stream of cumene 12 is provided under pressure to an oxidation station 14 where cumene is first oxidized in air to form CHP (cumene hydroperoxide) at very high yield with cumene conversion in the range of about 20 to 42% per-pass. No catalyst is used for this step in the process other than the CHP itself which is autocatalytic and does not require (and is highly undesirable) to have other acids present in the reactor. A portion of the effluent from the oxidation station 14 is transferred through line 15 to a concentration station 16 where the CHP concentration is raised to a level of about 80 to 85 wt %. A portion of uncoverted cumene is recycled through line 17 back to the supply line 12 and is fed again through the oxidation station 14.

The concentrated CHP is transferred through line 21 from the concentration section 16 to a decomposition (e.g., cleavage) station 18 where the CHP is catalytically decomposed using dilute mineral acid (e.g., $H_2SO_4$) to phenol and acetone under very carefully controlled temperature, acid concentration, water, and residence time to ensure that essentially complete conversion of CHP occurs. Failure to achieve complete conversion of CHP to phenol and acetone risks the build up of the CHP to a level which can be explosive in nature. Thus this section is very critical for safety, reliability, and overall yield performance standpoint.

A portion of the effluent from the decomposition station 18 is transferred through line 23 to a neutralization station 20 where the decomposition station effluent is contacted with a neutralizing agent provided through line 24. The neutralizing agent typically is 2-methylpentamethylenediamine (Dytek), hexamethylenediamine, triethylenetetramine, or diethylenetriamine.

Upon sufficient neutralization an effluent is delivered from the neutralization station 20 to a product recovery and purification station 26 where acetone and phenol are purified and recovered respectively in stations 26 and 28a, b. A portion of the phenol recovered is recirculated through line 29 back to the neutralization station 20. Followed by the isolation, hydrogenation and purification of AMS in station 30. Unreacted cumene is transferred from the AMS station 30 through recycle line 32 back to mix with the cumene feed line 12 and passed again through the connected stations.

Figure 3:
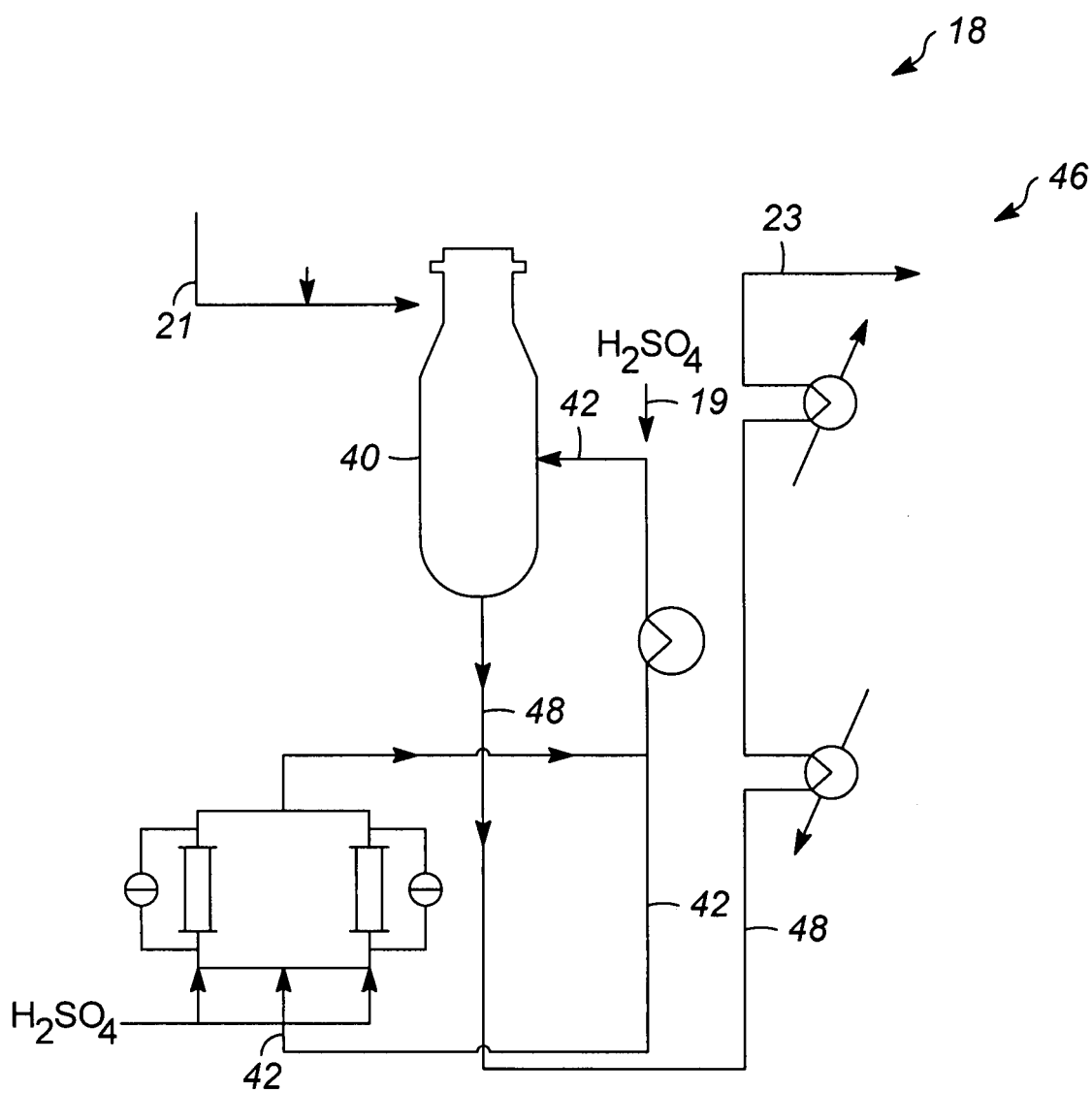
FIG. 3 shows a flow diagram for the decomposition section of the prior art process.
Figure 4:
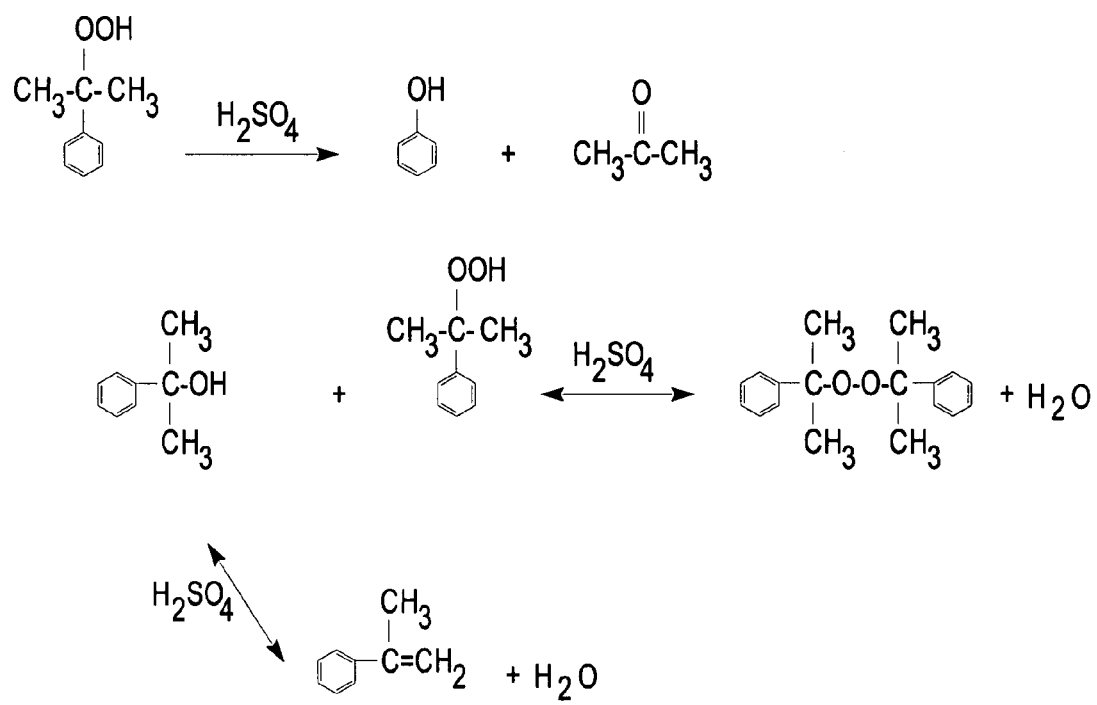
FIGS. 4 and 5 show the reactions occurring during the dehydration step of the prior art process that follows the main decomposer reactor to convert major side products such as DCP and DMPC to additional CHP and AMS respectively for recycle to phenol.
Figure 5:
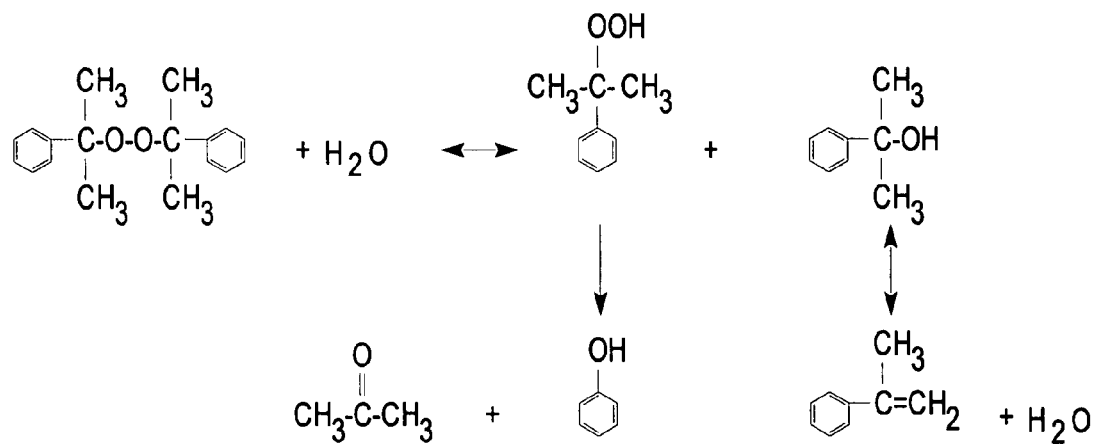

FIG. 3 shows a flow diagram for the decomposition station or section 18 of the plant. The decomposition section 18 is where a two step process shown in FIG. 4 is carried out. The decomposition station 18 has a decomposer vessel 40 where CHP is converted to phenol and acetone at about 60° C. to 70° C. using about 20 to 60 ppm liquid $H_2SO_4$ as a catalyst supplied through line 19. A high recycle ratio (e.g., 25/1 to 100/1) of decomposer effluent to feed through a decomposer loop 42 is used to control heat and ensure conversion from about 85 wt % CHP down to about 1 to 2.5 wt % CHP. A dehydrator 46 receives a portion of the effluent from the decomposer through line 48 where DCP (dicumylperoxide) is converted to CHP and DMPC (dimethylphenylcarbinol) and DMPC is subsequently dehydrated to form AMS (alpha-methylstyrene) in high yield (See FIGS. 4 and 5). This later allows AMS to be hydrogenated back to cumene and recycled in the process to reduce the fresh cumene feed consumption.

The present invention provides a process for decomposing CHP without the use of $H_2SO_4$, or other liquid mineral acid, as a catalyst. The decomposition of CHP is catalyzed by a solid acid catalyst, more preferably by a layered acid catalyst and most preferably a layered acid catalyst in particle form. It is believed that the use of a layered catalyst particle may limit the reaction path, and thereby minimize the undesirable products and thus enhance the selectivity and stability. The CHP decomposition is extremely fast, diffusionally limited, and prone to formation of heavy condensed oxygenated by-products which tend to condense further if not desorbed from the surface of the catalyst very quickly.

The solid acid catalyst particles has a layered structure with an inner core and an outer layer of a zeolite beta having a volumetric fraction from about 0.17 to about 0.62 of the entire catalyst particle, more preferably from about 0.235 to about 0.503, and most preferably from about 0.289 to 0.503. Also, in a preferred form of the invention, the inner core and outer layer form a generally, but not limited to, spherical particle having an average diameter of from 0.1 mm to 5.5 mm, and more preferably from 0.7 mm to about 3 mm.

The inner core material is selected from, for example, refractory inorganic oxides, silicon carbide and metals. Examples of refractory inorganic oxides include without limitation alpha alumina, gamma alumina, theta alumina, chi alumina, cordierite, zirconia, titania and mixtures thereof. Preferred inorganic oxides include alpha alumina, gamma alumina, chi alumina and cordierite.

The materials that form the inner core can be formed into a variety of shapes such as pellets, extrudates, spheres, rings, trilobes, saddles, or other physical forms known in the art. Of course, not all materials can be formed into each shape. Preparation of the inner core can be done by means known in the art such as oil dropping, pressure molding, metal forming, pelletizing, granulation, extrusion, rolling methods and marumerizing. A spherical inner core is commonly used, although pressure drop considerations can warrant the use of shaped particles that result in a higher void fraction when such shapes are packed into a catalyst bed. The inner core whether spherical or not has an effective diameter of about 0.05 mm to about 5 mm and preferably from about 0.4 mm to about 3 mm. For a non-spherical inner core, effective diameter is defined as the diameter the shaped particle would have if it were molded into a sphere. Once the inner core is prepared, it is calcined at a temperature of about 400° C. to about 1500° C.

The inner core is now coated with the zeolite beta outer layer. The composition, structure and method of synthesis of zeolite beta is described in U.S. Pat. No. 3,308,069.

The outer layer is applied by forming a slurry of the zeolite beta powder and then coating the inner core with the slurry by means well known in the art. To form a layered composition in which the outer layer is a zeolite beta bound with an inorganic metal oxide, the slurry will contain an appropriate sol, or carrier material, of the binder used for suspending the zeolite beta. In the case of incorporating alumina, silica, magnesia, zirconia or titania binders into the zeolite beta for producing the outer layer of the composition, it is appropriate to use a hydrosol. For example, any of the aluminas can be mixed with water and an acid such as nitric, hydrochloric, or sulfuric to give an aluminum sol. Alternatively, an aluminum sol can be made by for example, dissolving aluminum metal in hydrochloric acid and then mixing the aluminum sol with the alumina powder. When the alumina powder is desired, it is also possible to use a solution of boehmite or aluminum nitrate in place of the aluminum sol.

Types of silica sols used to form a silica bound zeolite beta are commercially available as aquasols or organosols containing dispersed colloidal silica particles. Otherwise, a silica gel may be used to ultimately form a silica binder in the zeolite beta outer layer. If a magnesia binder is desired, the starting slurry will contain hydrolyzed magnesium alkoxide. When a zirconia binder is used for the outer layer preparation, the preferred starting acidic sol is an aqueous zirconium acetate solution, which is preferably combined with an urea gelling agent. When a titania binder is used, the acidic sol is preferably a solution of titanyl oxychloride, which is also preferably combined with an urea gelling agent. The amount of sol added to the slurry is based on typical binder contribution from about 10% to about 50% of the weight of the bound zeolite beta forming the outer layer of the composition. Those skilled in the art will readily appreciate the relationship between the zeolite beta:sol weight ratio of the slurry and the concentration of binder in the resulting outer layer.

It is also preferred that the slurry contain an organic bonding agent that 1) aids in the adhesion of the layer material (i.e. the bound zeolite beta) to the inner core; and 2) improves the overall strength of the outer layer zeolite beta/binder system. Examples of this organic bonding agent include, but are not limited to, polyvinyl alcohol (PVA), hydroxylpropyl cellulose, methyl cellulose and carboxy methyl cellulose. The amount of organic bonding agent which is added to the slurry will vary considerably from about 0.1% to about 5% by weight of the slurry. How strongly the outer layer is bonded to the inner core can be measured by the amount of layer material lost during an attrition test, i.e., attrition loss. Loss of the zeolite beta outer layer by attrition is measured by agitating the catalyst, collecting the fines and calculating an attrition loss. It has been found that by using an organic bonding agent as described above, the attrition loss is less than about 25% by weight of the outer layer. In most cases, this attrition loss is less than 10%. Physical strength of the catalyst particles is critical in the proposed CHP decomposition process where the solid catalyst particles are introduced to the decomposer as a slurry, colloidal mixture or otherwise suspended solid/liquid mixture.

Depending on the particle size of the zeolite beta outer layer, it may be necessary to mill the slurry in order to reduce the particle size and simultaneously give a narrower particle size distribution. This can be done by means known in the art such as ball milling for times of about 30 minutes to about 5 hours and preferably from about 1.5 hours to about 3 hours. It is believed that using a slurry with a particle size distribution that has been adjusted in this manner improves the bonding of the outer layer to the inner core. It should be also noted that, in addition to the zeolite beta powder, sol of the binder, and bonding agent, the slurry will contain a balance of de-ionized water. The amount of water is often adjusted after any milling operation in order to obtain a viscosity of the slurry in the range from about 30 to about 600 centipoise.

Without wishing to be constrained by any particular theory, it is believed that the organic bonding agent aids in providing a high-density, mechanically-superior zeolite beta/binder system that is used to form the outer layer. Furthermore, it appears that bonding agents such as PVA aid in making an interlocking bond between the outer layer material and the inner core. Whether this occurs by the PVA reducing the surface tension of the core or by some other mechanism is not clear. What is clear is that a considerable reduction in loss of the outer layer by attrition is observed with the use of a bonding agent. This desirable characteristic, therefore, results from a combination of a structurally improved zeolite beta/binder system as well as an enhanced bond between the outer layer and inner core, both of which are attributable to the use of the organic bonding agent.

Coating of the inner core with the slurry can be accomplished by means such as rolling, dipping, spraying, etc., to yield a coated core having an outer layer. One preferred coating technique involves using a fixed fluidized bed of inner core particles and spraying the slurry into the bed to coat the particles evenly. The thickness of the layer of the coated core can vary considerably, but usually the thickness is in a range that outer layer will take up a volumetric fraction of the particle from about 0.17 to about 0.62, more preferably from about 0.235 to about 0.503, and most preferably from about 0.289 to 0.503. It should be pointed out that the optimum layer thickness will depend on the specific process design of the decomposition section of the unit.

Once the inner core is coated with the outer bound zeolite beta layer, the resultant coated core is dried at a temperature of about 50° C. to about 300° C. for a time of about 1 hour to about 24 hours to provide a dried coated core. Subsequently, the dried coated core is calcined at a temperature of about 400° C. to about 900° C. for a time of about 0.5 hour to about 10 hours to effectively bond the outer layer to the inner core and provide the layered catalyst particle of the present invention. The calcination step also removes any remaining organic template material within the zeolite beta as well as any residual bonding agent. In some cases, the catalyst may be activated in a modified calcination step wherein the organic template is first decomposed in a flow of pure nitrogen. The oxygen concentration is then gradually increased to combust any residual hydrocarbons in the zeolite beta. It is also possible to combine the drying and calcining operations into a single step.

The following example is presented in illustration of this invention and is not intended as undue limitations on the generally broad scope of the invention as set forth in the appended claims.

EXAMPLE 1

The preparation of zeolite beta layered catalysts with different thicknesses on inner cores of varying diameters for testing in Runs 1 through 12 as set forth in Table 1 followed procedure described in U.S. Pat. No. 6,710,003, and was illustrated by the procedure described as follow. More particularly a solution of polyvinyl alcohol (PVA) bonding agent (20% by weight), aluminum sol (20% by weight) and de-ionized water (balance) was prepared and mixed for 15 minutes. A pre-weighed amount of zeolite beta powder was blended into this solution and the resulting slurry was stirred for 15 minutes. The amount of zeolite beta used was based on obtaining a final outer layer comprising 70% by weight zeolite and 30% by weight alumina binder, resulting from the incorporation of aluminum sol. A more uniform composition was obtained by ball milling the slurry for two hours, after which the viscosity was adjusted to about 100 centipoise by adding a further amount of de-ionized water.

A fixed fluidized bed of gamma alumina particles having an average diameter of about 1.6 mm were then sprayed with the slurry to provide an even coating. After the coating step, the material was dried at a temperature of 100° C., and thereafter at 350° C. for one hour and at 630° C. for two hours in flowing air prior to use in CHP decomposition tests. The calcination serves to remove remaining organic template and PVA, as well as to convert the alumina sol into gamma alumina. The resulting catalyst has an outer layer thickness of from 37 µm to 240 µm and a volumetric fraction from 0.16 to 0.63 and as shown in Table 1 below. Very good layer physical strength, as determined by subjecting the resulting layered composition to an attrition test, was achieved using this preparation method. A relative attrition value of about 1.0 was typically observed.

The catalysts were tested using the following experimental set up. Approximately 4 gms of catalyst was added to 36 cc of a 1:1 molar mixture of acetone/phenol in a 50 cc stirred glass vessel operating as a continuous stirred tank reactor (CSTR) system to simulate the environment of a commercial decomposer reactor. The temperature of the mixture is then raised to about 55° C. to 70° C. and approximately 4 gms of an 85 wt % CHP concentrate solution derived from a commercial phenol unit (see reference numeral 21 of FIG. 1) as a source of fresh CHP feed is injected into the reaction mixture in about 30 seconds. Reaction products and temperature were monitored during the course of the runs to determine the extent of reaction and the product selectivity over an approximately 25 min of total reaction time. A continuous circulation of the reaction products was maintained throughout the course of the run to control the strong exothermic heat of reaction that occurs and to simulate CSTR reactor conditions. Results obtained are described as followed with detailed product yields and selectivities shown in Table 1 at reaction time of 25 minutes.

TABLE 1

| Run # | Core Material | Core Diameter (μm) | Outer Layer-Zeolite beta Thickness (μm) | Outer Layer-Zeolite beta Volume Fraction | Residual CHP (%) t = 25 min | End of Run AMS Yield (%) | End of Run AMS Selectivity (%) |
|---|---|---|---|---|---|---|---|
| 1 | gamma-Al$_2$O$_3$ | 1638 | 48 | 0.157 | 58.5 | 21.6 | 72.0 |
| 2 | gamma-Al$_2$O$_3$ | 1638 | 48 | 0.157 | 32.9 | 58.9 | 85.6 |
| 3 | gamma-Al$_2$O$_3$ | 1638 | 48 | 0.157 | 25.3 | 69.4 | 89.6 |
| 4 | gamma-Al$_2$O$_3$ | 1638 | 48 | 0.157 | 13.3 | 77.3 | 88.7 |
| 5 | gamma-Al$_2$O$_3$ | 1638 | 103 | 0.299 | 0.0 | 86.9 | 91.5 |
| 6 | gamma-Al$_2$O$_3$ | 1638 | 103 | 0.299 | 0.0 | 86.3 | 91.4 |
| 7 | alpha-Al$_2$O$_3$ | 1079 | 65 | 0.289 | 0.0 | 85.6 | 88.9 |
| 8 | alpha-Al$_2$O$_3$ | 1079 | 135 | 0.488 | 0.0 | 82.2 | 85.4 |
| 9 | chi-Al$_2$O$_3$ | 1829 | 165 | 0.392 | 0.0 | 80.9 | 83.6 |
| 10 | chi-Al$_2$O$_3$ | 1839 | 240 | 0.503 | 0.0 | 82.4 | 86.2 |
| 11 | gamma-Al$_2$O$_3$ | 794 | 37 | 0.235 | 0.0 | 80.2 | 82.9 |
| 12 | gamma-Al$_2$O$_3$ | 794 | 157 | 0.632 | 0.0 | 68.5 | 71.4 |

The zeolite beta layered catalysts are active under conditions similar to what is currently being practiced for a state-of-the-art decomposer design (e.g., 55 to 70° C. (131-158° F.) and 25 min residence time using trace sulfuric acid.)

Alumina bound zeolite beta layers with an intermediate volumetric fraction from about 0.289 to 0.503 gave the highest yields. The catalyst having a layer of lower volumetric fractions showed low CHP conversion activity (Runs 1-4), while the one having a layer with a high volumetric fraction gave high activity, but significantly poor selectivity to the desirable product (Run 12).

Best results observed in this testing are better than any known commercial decomposer operation using trace sulfuric acid with AMS yields ranging from 78 to about 81% and an overall cumene/phenol consumption ratio of about 1.31. Note that Run 5 showed an AMS yield in excess of 86% which is equivalent to an overall cumene/phenol consumption ratio of about 1.29 if the resultant AMS is hydrogenated and recycled as cumene back to the oxidation section of the process which is typically what is practiced in commercial operation. The only way, known to the inventors hereof, to achieve such a yield with the conventional sulfuric acid technology is to use acetone recycled as a diluent in the decomposer section (at molar ratio significantly greater than 1) which would be at an added cost and is typically difficult to justify.

We have discovered that the use of a layered beta zeolite catalyst not only produces surprising results but is also optimized with a outer layer having a volumetric ratio from about 0.17 to about 0.62, more preferably from about 0.235 to 0.503, and most preferably from about 0.289 to 0.503 of the entire catalyst particle.

The foregoing description, drawings and illustrative embodiment clearly illustrate the advantages encompassed by the process of the present invention and the benefits to be afforded with the use thereof.

What is claimed is:

1. A catalyst particle comprising an inner core, an outer layer surrounding and bonded to the inner core selected from silicon carbide, metals and refractory inorganic oxides, wherein the refractory inorganic oxides are selected from the group consisting of alpha alumina, gamma alumina, theta alumina, chi alumina, zirconia, and titania and mixtures thereof, the outer layer comprising a zeolite beta catalyst, and the outer layer having a volumetric fraction from about 0.289 to about 0.62 of the entire catalyst particle.

2. The catalyst particle of claim 1 wherein the outer layer has a volumetric fraction from about 0.289 to 0.503 of the entire catalyst particle.

3. The catalyst particle of claim 1 wherein the inner core and the outer layer form a generally spherical particle having a average particle diameter of from about 0.1 mm to about 5.5 mm.

4. The catalyst particle of claim 1 wherein the outer layer further comprising a binder material of an inorganic metal oxide.

5. The catalyst particle of claim 4 wherein the inorganic metal oxide is selected from the group consisting of alumina, silica, magnesia, titania and zirconia.

6. A catalyst particle comprising a core of a refractory inorganic oxide selected from the group consisting of alpha alumina, gamma alumina, theta alumina, chi alumina, zirconia, and titania and mixtures thereof, a zeolite beta coating surrounding the core, the zeolite beta layer having a volumetric fraction from about 0.289 to about 0.503 of the entire catalyst particle.

7. The catalyst particle of claim 6 wherein the inner core and the outer layer form a generally spherical particle having a average particle diameter of from about 0.1 mm to about 5.5 mm.

8. The catalyst particle of claim 6 wherein the outer layer further comprising a binder material of an inorganic metal oxide.

9. The catalyst particle of claim 8 wherein the inorganic metal oxide is selected from the group consisting of alumina, silica, magnesia, titania and zirconia.

10. A process for preparing a layered catalyst particle comprising:
providing an inner core selected from silicon carbide, metals and refractory inorganic oxides, wherein the refractory inorganic oxides are selected from the group consisting of alpha alumina, gamma alumina, theta alumina, chi alumina, zirconia, and titania and mixtures thereof;
providing a coating material of a zeolite beta;
providing a sol of a binder material;
preparing a slurry by mixing the coating material, the sol of the binder material and an organic bonding agent;
coating the inner core with the slurry to yield a coated core;
drying the coated core at a temperature from about 50° C. to about 300° C. to yield a dried coated core; and,
calcining the dried coated core at a temperature from about 400° C. to about 900° C. for a time sufficient to bond the coating material to the inner core to provide the layered catalyst particle having an outer layer having a volumetric fraction from about 0.289 to about 0.62 of the entire catalyst particle.

11. The process of claim 10 wherein the outer layer has a volumetric fraction from about 0.289 to 0.503 of the entire catalyst particle.

* * * * *